US00PP21532P2

(12) United States Plant Patent
Meilland

(10) Patent No.: US PP21,532 P2
(45) Date of Patent: Nov. 30, 2010

(54) ***FLORIBUNDA* ROSE PLANT NAMED 'MEIJECYCKA'**

(50) Latin Name: *Rosa hybrida*
Varietal Denomination: Meijecycka

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/458,257

(22) Filed: Jul. 7, 2009

(51) Int. Cl.
*A01H 5/00* (2006.01)

(52) U.S. Cl. ..... Plt./145

(58) Field of Classification Search ..... Plt./145
See application file for complete search history.

*Primary Examiner*—Susan B McCormick Ewoldt
(74) *Attorney, Agent, or Firm*—Buchanan Ingersoll & Rooney PC

(57) ABSTRACT

A new and distinct Floribunda rose plant is provided which abundantly and nearly continuously forms attractive yellow cup-shaped blossoms commonly displaying approximately 5 to 7 petals. The growth habit is bushy and the adult plant commonly assumes a generally hemispherical configuration. The plant exhibits very strong vegetation, with green semi-glossy foliage that contrasts nicely with the yellow bossom coloration. The blossoms display no fragrance. The new variety is well suited for growing as attractive ornamentation in parks and gardens.

1 Drawing Sheet

Figures 1, 2, 3, 4, 5, 6, 7, 8, 9, 10, 11, 12, 13, 14, 15, 16, 17:
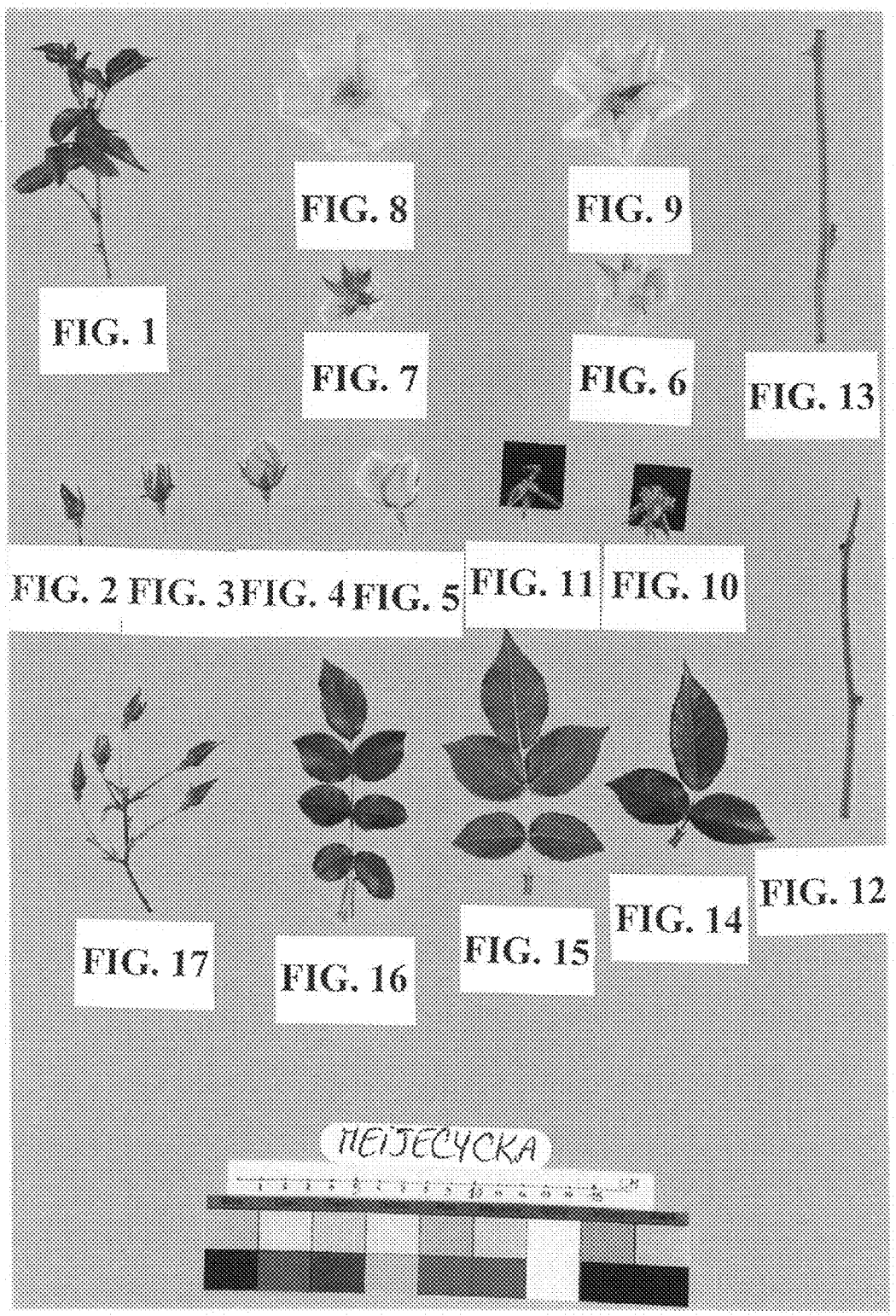

Botanical/commercial classification: *Rosa hybrida*/Floribunda Rose Plant.

Varietal denomination: cv. Meijecycka.

SUMMARY OF THE INVENTION

The new variety of *Rosa hybrida* Floribunda rose plant was created by artificial pollination wherein two parents were crossed which previously had been studied in the hope that they would contribute the desired characteristics. The female parent (i.e., the seed parent) was a product of the cross of 'The Fairy' variety (non-patented in the United States) and an unnamed seedling (non-patented in the United States). The male parent (i.e., the pollen parent) was the product of the cross of the 'Kortikel' variety (non-patented in the United States) and the 'Macshana' variety (U.S. Plant Pat. No. 5,427). The parentage of the new variety can be summarized as follows:

('The Fairy'×Unnamed Seedling)×('Kortikel'×Macshana').

The seeds resulting from the above pollination were sown and small plants were obtained which were physically and biologically different from each other. Selective study resulted in the identification of a single plant of the new variety.

It was found that the new Floribunda rose plant of the present invention:

(a) exhibits a bushy adult growth habit that commonly is generally hemispherical in configuration, (b) abundantly and nearly continuously forms attractive yellow cup-shaped blossoms commonly displaying approximately 5 to 7 petals, (c) forms very strong vegetation with attractive green semi-glossy foliage that contrasts nicely with the yellow blossom coloration, and (d) is well suited for growing as ornamentation in parks and gardens.

The new variety well meets the needs of the horticultural industry and can be grown to advantage in the landscape where attractive ornamentation is desired. The attractive yellow blossoms commonly initiate blossoming early in the season.

The new variety can be readily distinguished from its ancestors. For instance, 'The Fairy' variety displays dissimilar light pink blossoms. The blossoms of the 'Kortikel' and 'Macshana' varieties commonly possess a substantially larger number of petals than the new variety. The product of the cross of 'The Fairy' and unnamed seedling (non-patented in the United States) displays very pale yellow blossoms and a slow repeat blooming characteristic. The product of the cross of the 'Kortikel' and 'Machana' varieties (non-patented in the United States) displays blossoms having a dissimilar very intense yellow coloration. The new variety also can be readily distinguished from the 'Medresia' variety (non-patented in the United States) and the 'Meibaltaz' variety (U.S. Plant Pat. No. 8,449). The 'Medresia' and 'Meibaltaz' varieties display blossoms having considerably more petals. Also, the blossom coloration of the 'Meidresia' variety is more intense, and the 'Meibaltaz' variety exhibits a more upright growth habit.

The new variety has been found to undergo asexual propagation in France at Le Cannet-des-Maures, by a number of routes, including budding, grafting, and the use of cuttings. Asexual propagation by the above-mentioned techniques in France has shown that the characteristics of the new variety are stable and are strictly transmissible by such asexual propagation from one generation to another. Accordingly, the new variety undergoes asexual propagation in a true-to-type manner.

The new variety has been named 'Meijecycka'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately one year of age and were observed during May while growing on their own roots outdoors at Le Cannet des Maures, Var, France. Dimensions in centimeters are indicated at the bottom of the photograph together with comparative color information.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—upper surface;

FIG. 15—illustrates a specimen of a leaf with five leaflets—plan view—under surface;

FIG. 16—illustrates a leaf with seven leaflets—plan view—upper surface; and

FIG. 17—illustrates a specimen of a cluster of buds.

DETAILED DESCRIPTION

The chart used in the identification of the colors is that of The Royal Horticultural Society (R.H.S. Colour Chart), London, England. Common color terms are to be accorded their customary dictionary significance. The description is based on the observation of one-year-old plants during October while growing on their own roots outdoors at Le Cannet des Maures, Var, France.

Class: Floribunda.

Plant:

*Habit.*—Bushy, commonly in a rounded generally hemispherical configuration.

*Height.*—Commonly approximately 70 cm on average at the end of the growing season.

*Width.*—Commonly approximately 70 cm on average at the end of the growing season.

Branches:

*Color.*—Young stems: near Green Group 143C and sometimes with some anthocyanin coloration of Greyed-Red Group 178A. Adult wood: near Yellow-Green Group 146B.

*Stem length.*—Commonly approximately 60 to 65 cm on average.

*Stem diameter.*—Commonly approximately 8 mm on average.

*Stem number.*—Commonly approximately four on average.

*Thorns.*—On young stems: Small prickles: commonly absent. Long prickles: configuration: elongated and longish-pointed on the upper surface, and hooked on the under surface with an oval, long, and narrow base. quantity: approximately 5 on average on a stem length of 10 cm. length: approximately 0.7 cm on average. color: near Greyed-Orange Group175B. On adult stems: Small prickles: commonly absent. Long prickles: configuration: rather upright and rather elongated on the upper surface, and slightly concave on the under surface with an oval, long, and narrow base. quantity: approximately 9 on average on a stem length of 18 cm. length: approximately 0.7 cm on average. color: near Greyed-Orange Group 176C.

Leaves:

*Stipules.*—Adnate, pectinate, and broad, approximately 2.5 cm in length on average, approximately 0.8 cm in width on average, near Green Group 141B on the upper surface, and near Green Group 143A on the under surface.

*Petioles.*—Upper surface: near Green Group 137C in coloration. Under surface: near Yellow-Green Group 146B in coloration. Texture: commonly slightly glandular on the upper surface and commonly bear some prickles on the under surface. Length: approximately 3.8 cm for the terminal leaflet.

*Rachis.*—Upper surface: near Yellow-Green Group 146B in coloration. Under surface: near Yellow-Green Group 144B in coloration. Texture: commonly bear some prickles.

*Leaflets.*—Number. 3 and most often 5 and 7. Shape: generally oval with a rounded base and an acuminate tip. Size: the terminal leaflets commonly are approximately 5.2 cm in length on average, and approximately 3.2 cm in width on average. Serration: small and single (as illustrated). Texture: smooth on upper and under surfaces, relatively thick and semi-glossy on the upper surface. General appearance: rather dense. Color (young foliage): upper surface: near Green Group 143A. under surface: near Green Group 143B. Color (adult foliage): upper surface: near Green Group 141A. under surface: near Yellow-Green Group 146B.

Inflorescence:

*Number of flowers.*—Pluriflorous, commonly in clusters of approximately 6 to 12 flowers per stem.

*Peduncle.*—Smooth, near Green Group 143C in coloration, approximately 3.2 cm in length on average, and approximately 0.2 cm in diameter on average.

*Sepals.*—Upper surface: tomentose and near Green Group 137C in coloration. under surface: smooth and near Green Group 143A in coloration. Configuration: approximately 2.7 cm in length on average, approximately 0.7 cm in width on average at the widest point, and longish-pointed at the tip and narrow with an upright base.

*Buds.*—Shape: elongated. Size: small. Length: approximately 1.5 cm on average. Width: approximately 0.8 cm on average at the widest point. Color upper surface: near Yellow Group 5A as the calyx breaks. under surface: near Yellow Group 6A as the calyx breaks.

*Flower.*—Shape: cup-shaped. Diameter approximately 7 cm on average when open. Color (in the course of opening): upper surface: near Yellow Group 7A. under surface: near Yellow Group 9A. Color (when fully open): upper surface: near Yellow Group 3B.

under surface: Yellow Group 5C. Fragrance: none. Petal number: commonly approximately 5 to 7 on average under normal growing conditions. Petal shape: generally with a cuneiform tip and a rounded base. Petal size: commonly approximately 3.5 cm in length on average, and approximately 3.7 cm in width on average. Petal texture: smooth, and flexible. Petal arrangement: imbricated, and without petaloids. Petal drop: good with the petals commonly detaching cleanly before drying. Stamen number: approximately 106 on average. Anthers: regularly arranged around the styles, approximately 0.2 cm in size on average, and near Yellow-Orange Group 15B in coloration. Pollen: present. Filaments: approximately 0.5 cm in length on average, and near Yellow Group 6A in coloration. Pistils: approximately 19 on average. Stigmas: approximately 0.1 cm in size on average, and near Yellow-Green Group 150D in coloration. Styles: approximately 1 cm in length on average, and near Yellow-Green Group 150D in coloration. Receptacle: smooth, pitcher-shaped in longitudinal section, approximately 0.6 cm in length on average, approximately 0.6 cm in width on average at the widest point, and near Green Group 143B in coloration.

Development:

*Vegetation.*—Very strong.

*Blooming.*—Very early, very abundant and nearly continuous.

*Tolerance to diseases.*—Normal, with no particular problem having been observed during observations to date.

I claim:

1. A new and distinct Floribunda rose plant characterized by the following combination of characteristics:

(a) exhibits a bushy adult growth habit that commonly is generally hemispherical in configuration, (b) abundantly and nearly continuously forms attractive yellow cup-shaped blossoms commonly displaying approximately 5 to 7 petals, (c) forms very strong vegetation with attractive green semi-glossy foliage that contrasts nicely with the yellow blossom coloration, and (d) is well suited for growing as ornamentation in parks and gardens;

substantially as herein shown and described.

* * * * *

MEIJECYCKA